US009421650B2

(12) United States Patent
Bienvenu et al.

(10) Patent No.: US 9,421,650 B2
(45) Date of Patent: Aug. 23, 2016

(54) METHOD OF FORMING A DRUG-ELUTING MEDICAL DEVICE

(71) Applicant: Medtronic Vascular, Inc., Santa Rosa, CA (US)

(72) Inventors: Ryan Bienvenu, Santa Rosa, CA (US); John Kantor, Healdsburg, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 390 days.

(21) Appl. No.: 13/955,209

(22) Filed: Jul. 31, 2013

(65) Prior Publication Data

US 2014/0007406 A1     Jan. 9, 2014

Related U.S. Application Data

(62) Division of application No. 12/884,272, filed on Sep. 17, 2010, now Pat. No. 8,616,040.

(51) Int. Cl.
*A61F 2/86* (2013.01)
*B23P 19/04* (2006.01)
*A61M 31/00* (2006.01)
(Continued)

(52) U.S. Cl.
CPC . *B23P 19/04* (2013.01); *A61F 2/86* (2013.01); *A61F 2/88* (2013.01); *A61L 31/022* (2013.01); *A61L 31/16* (2013.01); *A61M 31/002* (2013.01); *A61F 2250/0068* (2013.01); *A61L 2400/18* (2013.01); *Y10T 29/4987* (2015.01)

(58) Field of Classification Search
CPC ............... A61F 2/06; A61F 2/86; A61F 2/88; A61F 2/91; A61F 2250/0068; A61M 25/003; A61M 31/002; A61M 2039/082; B23P 19/04; A61L 31/16

See application file for complete search history.

(56) References Cited

U.S. PATENT DOCUMENTS 2,153,936 A    4/1939   Owens et al.
2,241,518 A    5/1941   Offutt
(Continued)

FOREIGN PATENT DOCUMENTS

EP    836839 A2   10/1997
EP    1600534     11/2005
(Continued)

OTHER PUBLICATIONS

U.S. Appl. No. 09/716,146, filed Nov. 17, 2000, Boyle.
(Continued)

*Primary Examiner* — Edward Tolan (57) ABSTRACT

A method of forming a stent includes the steps of forming a composite member into a stent pattern, forming openings through an outer member of the composite member, processing the composite member to remove a portion of the composite member without adversely affecting the outer member, and swaging the outer member to create a plurality of lumens. The composite member may be formed of an outer member with an hourglass-shaped inner member, wherein the processing step removes the inner member and the swaging step forms two lumens from the hourglass shaped cavity. The composite member may be formed of an outer member, an inner member, and an intermediate member, wherein the processing step removes the intermediate member and the swaging step presses portions of the outer member into contact with the inner member to form two lumens separated by the inner member.

12 Claims, 9 Drawing Sheets

(51) Int. Cl.
  *A61F 2/88* (2006.01)
  *A61L 31/02* (2006.01)
  *A61L 31/16* (2006.01)

(56) References Cited

U.S. PATENT DOCUMENTS

| | | | |
|---|---|---|---|
| 3,591,915 A | 7/1971 | Roberts et al. | |
| 4,531,933 A | 7/1985 | Norton et al. | |
| 4,643,716 A | 2/1987 | Drach | |
| 4,720,384 A | 1/1988 | DiLuccio et al. | |
| 4,763,647 A | 8/1988 | Gambale | |
| 4,800,882 A | 1/1989 | Gianturco | |
| 4,813,925 A | 3/1989 | Anderson, Jr. | |
| 4,886,062 A | 12/1989 | Wiktor | |
| 4,913,683 A | 4/1990 | Gregory | |
| 5,019,090 A | 5/1991 | Pinchuk | |
| 5,020,214 A * | 6/1991 | Tsuruoka | G01F 1/68 29/611 |
| 5,063,935 A | 11/1991 | Gambale | |
| 5,133,732 A | 7/1992 | Wiktor | |
| 5,154,705 A | 10/1992 | Fleischhacker et al. | |
| 5,234,456 A | 8/1993 | Silvestrini | |
| 5,306,250 A | 4/1994 | March et al. | |
| 5,345,945 A | 9/1994 | Hodgson et al. | |
| 5,536,274 A | 7/1996 | Neuss | |
| 5,538,735 A | 7/1996 | Ahn | |
| 5,569,197 A | 10/1996 | Helmus et al. | |
| 5,605,162 A | 2/1997 | Mirzaee et al. | |
| 5,630,840 A | 5/1997 | Mayer | |
| 5,670,161 A | 9/1997 | Healy et al. | |
| 5,782,903 A | 7/1998 | Wiktor | |
| 5,795,318 A | 8/1998 | Wang et al. | |
| 5,824,045 A | 10/1998 | Alt | |
| 5,843,117 A | 12/1998 | Alt et al. | |
| 5,882,335 A | 3/1999 | Leone et al. | |
| 5,891,108 A | 4/1999 | Leone et al. | |
| 5,902,266 A | 5/1999 | Leone et al. | |
| 5,941,118 A | 8/1999 | Tseng | |
| 5,957,903 A | 9/1999 | Mirzaee et al. | |
| 6,022,369 A | 2/2000 | Jacobson et al. | |
| 6,063,101 A | 5/2000 | Jacobsen et al. | |
| 6,071,305 A | 6/2000 | Brown et al. | |
| 6,099,561 A | 8/2000 | Alt | |
| 6,101,858 A | 8/2000 | Tseng | |
| 6,136,023 A | 10/2000 | Boyle | |
| 6,203,732 B1 * | 3/2001 | Clubb | A61F 2/91 164/464 |
| 6,206,915 B1 * | 3/2001 | Fagan | A61F 2/07 623/1.15 |
| 6,248,190 B1 | 6/2001 | Stinson | |
| 6,358,276 B1 | 3/2002 | Edwin | |
| 6,471,721 B1 | 10/2002 | Dang | |
| 6,478,778 B1 | 11/2002 | Jacobsen et al. | |
| 6,497,709 B1 | 12/2002 | Heath | |
| 6,558,422 B1 | 5/2003 | Baker et al. | |
| 6,623,519 B2 | 9/2003 | Edwin | |
| 6,641,607 B1 | 11/2003 | Hossainy et al. | |
| 6,656,162 B2 | 12/2003 | Santini, Jr. et al. | |
| 6,699,281 B2 | 3/2004 | Vallana et al. | |
| 6,752,829 B2 | 6/2004 | Kocur et al. | |
| 6,783,543 B2 | 8/2004 | Jang | |
| 6,989,071 B2 | 1/2006 | Kocur et al. | |
| 7,020,947 B2 * | 4/2006 | Bradley | B21C 1/003 29/458 |
| 7,041,130 B2 | 5/2006 | Santini, Jr. et al. | |
| 7,044,965 B1 | 5/2006 | Spielberg | |
| 7,060,093 B2 | 6/2006 | Dang et al. | |
| 7,101,392 B2 | 9/2006 | Heath | |
| 7,122,048 B2 | 10/2006 | Dimatteo et al. | |
| 7,135,039 B2 | 11/2006 | De Scheerder et al. | |
| 7,288,084 B2 | 10/2007 | Li | |
| 7,344,563 B2 | 3/2008 | Vallana et al. | |
| 7,384,660 B2 | 6/2008 | Hossainy et al. | |
| 7,490,396 B2 | 2/2009 | Bradley | |
| 7,575,593 B2 | 8/2009 | Rea et al. | |
| 8,070,731 B2 | 12/2011 | Wenchell et al. | |
| 8,168,350 B1 * | 5/2012 | Eshraghi | H01M 8/0256 429/235 |
| 8,238,867 B1 * | 8/2012 | Khoini-Poorfard | H04B 1/16 330/254 |
| 8,252,044 B1 | 8/2012 | Boyle | |
| 8,252,048 B2 | 8/2012 | Smith | |
| 2002/0065548 A1 | 5/2002 | Birdsall et al. | |
| 2002/0087209 A1 | 7/2002 | Edwin et al. | |
| 2002/0103527 A1 | 8/2002 | Kocur et al. | |
| 2002/0138048 A1 | 9/2002 | Tuch | |
| 2003/0021825 A1 | 1/2003 | Pathak et al. | |
| 2003/0068353 A1 | 4/2003 | Chen et al. | |
| 2003/0125803 A1 | 7/2003 | Vallana et al. | |
| 2003/0208256 A1 | 11/2003 | Dimatteo et al. | |
| 2004/0006382 A1 | 1/2004 | Sohier | |
| 2004/0023339 A1 | 2/2004 | Karpas | |
| 2004/0024449 A1 | 2/2004 | Boyle | |
| 2004/0037889 A1 | 2/2004 | Richeal et al. | |
| 2004/0106984 A1 | 6/2004 | Stinson | |
| 2004/0133270 A1 | 7/2004 | Grandt | |
| 2004/0148012 A9 | 7/2004 | Jang | |
| 2005/0043783 A1 | 2/2005 | Amis et al. | |
| 2005/0055080 A1 | 3/2005 | Istephanous et al. | |
| 2005/0060020 A1 | 3/2005 | Jenson | |
| 2005/0070996 A1 | 3/2005 | Dinh et al. | |
| 2005/0080481 A1 | 4/2005 | Madda et al. | |
| 2005/0145307 A1 | 7/2005 | Shireman et al. | |
| 2005/0177226 A1 | 8/2005 | Banik et al. | |
| 2005/0186241 A1 | 8/2005 | Boyle et al. | |
| 2005/0208100 A1 | 9/2005 | Weber et al. | |
| 2005/0272806 A1 | 12/2005 | Falotico et al. | |
| 2005/0278016 A1 | 12/2005 | Welsh et al. | |
| 2006/0004437 A1 | 1/2006 | Jayaraman | |
| 2006/0064157 A1 | 3/2006 | Shanley | |
| 2006/0093729 A1 * | 5/2006 | Marx | A61L 27/306 427/2.27 |
| 2006/0122689 A1 | 6/2006 | Kocur et al. | |
| 2006/0129231 A1 | 6/2006 | De Scheerder et al. | |
| 2006/0147489 A1 | 7/2006 | Shanley et al. | |
| 2006/0155369 A1 | 7/2006 | Edwin et al. | |
| 2006/0212109 A1 | 9/2006 | Sirhan et al. | |
| 2006/0224234 A1 | 10/2006 | Jayaraman | |
| 2006/0224237 A1 | 10/2006 | Furst et al. | |
| 2007/0005124 A1 | 1/2007 | De Scheerder et al. | |
| 2007/0027531 A1 | 2/2007 | Dimatteo et al. | |
| 2007/0043423 A1 | 2/2007 | Grewe | |
| 2007/0055352 A1 | 3/2007 | Naimark et al. | |
| 2007/0061007 A1 | 3/2007 | Nolting | |
| 2007/0112417 A1 | 5/2007 | Shanley et al. | |
| 2007/0123805 A1 | 5/2007 | Shireman et al. | |
| 2007/0168021 A1 | 7/2007 | Holmes, Jr. et al. | |
| 2007/0173923 A1 | 7/2007 | Savage et al. | |
| 2007/0219628 A1 | 9/2007 | Shanley et al. | |
| 2007/0282419 A1 | 12/2007 | Hilaire et al. | |
| 2008/0003251 A1 | 1/2008 | Zhou | |
| 2008/0051882 A1 | 2/2008 | Rubin | |
| 2008/0065201 A1 | 3/2008 | Li | |
| 2008/0077233 A1 | 3/2008 | Diaz et al. | |
| 2008/0183281 A1 | 7/2008 | Rea et al. | |
| 2008/0188925 A1 | 8/2008 | Zhao | |
| 2008/0195170 A1 | 8/2008 | Asgari | |
| 2008/0195196 A1 | 8/2008 | Asgari | |
| 2008/0234809 A1 | 9/2008 | Greenan | |
| 2008/0249599 A1 | 10/2008 | Allen et al. | |
| 2008/0255659 A1 | 10/2008 | Huang et al. | |
| 2008/0276935 A1 | 11/2008 | Wang | |
| 2008/0306579 A1 | 12/2008 | Dolan et al. | |
| 2009/0024209 A1 | 1/2009 | Ozdil et al. | |
| 2009/0024210 A1 | 1/2009 | Klocke et al. | |
| 2009/0035351 A1 | 2/2009 | Berglund et al. | |
| 2009/0061071 A1 | 3/2009 | McMorrow et al. | |
| 2009/0093871 A1 | 4/2009 | Rea et al. | |
| 2009/0132031 A1 | 5/2009 | Cook et al. | |
| 2009/0157172 A1 | 6/2009 | Kokate et al. | |
| 2009/0163995 A1 | 6/2009 | Shanley et al. | |
| 2009/0192593 A1 | 7/2009 | Meyer et al. | |
| 2009/0220612 A1 | 9/2009 | Perera | |
| 2009/0228095 A1 | 9/2009 | Shanley et al. | |

(56) References Cited

U.S. PATENT DOCUMENTS

| | | |
|---|---|---|
| 2009/0281615 A1 | 11/2009 | Kocur et al. |
| 2009/0312833 A1 | 12/2009 | Tittelbach et al. |
| 2009/0319026 A1 | 12/2009 | Meyer |
| 2010/0010621 A1 | 1/2010 | Klocke |
| 2010/0023115 A1 | 1/2010 | Robaina et al. |
| 2010/0036482 A1 | 2/2010 | Svrluga et al. |
| 2010/0057196 A1 | 3/2010 | Pathak |
| 2010/0070022 A1 | 3/2010 | Kuehling |
| 2010/0082096 A1 | 4/2010 | Gregorich |
| 2010/0145437 A1 | 6/2010 | Girton et al. |

FOREIGN PATENT DOCUMENTS

| | | |
|---|---|---|
| EP | 836839 B1 | 7/2006 |
| WO | WO94/18956 | 9/1994 |
| WO | WO96/19255 | 6/1996 |
| WO | WO96/26682 | 9/1996 |
| WO | WO98/23228 | 6/1998 |
| WO | WO00/01322 | 1/2000 |
| WO | WO02/060506 | 8/2002 |
| WO | WO03/092547 | 11/2003 |
| WO | WO2007/021749 | 2/2007 |

OTHER PUBLICATIONS

U.S. Appl. No. 12/428,581, filed Apr. 23, 2009, Hoff et al.
U.S. Appl. No. 12/500,359, filed May 30, 2002, Storment et al.
Basarir et al., "Osseointegration in Arthroplasty: Can Simvastatin Promote one response to Implants?" International Orthopedics (SICOT) (2009) 33:855-859.
Berger "Coating Drug-Eluting Arterial Stents Using Ultrasonic Spray Nozzle" ILASS Americas, 19$^{th}$ Annual Conference on Liquid Atomization and Spray Systems, May 2006.
Derle et al., "Particle Engineering Techniques to Enhance Dissolution of Poorly Water Soluble Drugs" International Journal of Current Pharmaceutical Research, vol. 2, Issue 1, 2010, pp. 10-15.
Polacco et al. "Biodegradable Hollow Fibres Containing Drug-Loaded Nanoparticles as Controlled Release Systems" Polym International 51:1464-1472 (2002).
Purvis et al., "Cryogenic Liquids, Nanoparticles, and Microencapsulation" International Journal of Pharmaceutics, 2006.
"Supercritical Carbon-Dioxide Cleaning Defined" Supercritical Carbon-Dioxide Cleaning Technology Review, Jul. 1996.
PCT Search Report PCT/US2010/039087.
PCT Search Report PCT/US2010/049439.
PCT Search Report PCT/US2010/049437.
PCT Search Report PCT/US2010/049434.

* cited by examiner

METHOD OF FORMING A DRUG-ELUTING MEDICAL DEVICE

RELATED APPLICATIONS

This application is a Division of and claims the benefit of U.S. patent application Ser. No. 12/884,272 filed Sep. 17, 2010, the disclosures of which are herein incorporated by reference in their entirety.

FIELD OF THE INVENTION

The present invention relates to implantable medical devices that release biologically or pharmacologically active substances and methods of forming such medical devices.

BACKGROUND OF THE INVENTION

Drug-eluting implantable medical devices have become popular in recent times for their ability to perform their primary function (such as structural support) and their ability to medically treat the area in which they are implanted.

For example, drug-eluting stents have been used to prevent restenosis in coronary arteries. Drug-eluting stents may administer biologically or pharmacologically active substances such as anti-inflammatory compounds that block local invasion/activation of monocytes, thus preventing the secretion of growth factors that may trigger VSMC proliferation and migration. Other potentially anti-restenotic compounds include anti-proliferative agents, such as chemotherapeutics, which include rapamycin and paclitaxel. Other classes of drugs such as anti-thrombotics, anti-oxidants, platelet aggregation inhibitors and cytostatic agents have also been suggested for anti-restenotic use.

Drug-eluting medical devices may be coated with a polymeric material which, in turn, is impregnated with a biologically or pharmacologically active substance or a combination of biologically or pharmacologically active substances. Once the medical device is implanted at a target location, the biologically or pharmacologically active substance is released from the polymer for treatment of the local tissues. The biologically or pharmacologically active substance is released by a process of diffusion through the polymer layer for biostable polymers, and/or as the polymer material degrades for biodegradable polymers.

Controlling the rate of elution of a biologically or pharmacologically active substance from the impregnated polymeric material is generally based on the properties of the polymer material. However, at the conclusion of the elution process, the remaining polymer material in some instances has been linked to an adverse reaction with the vessel, possibly causing a small but dangerous clot to form. Further, drug impregnated polymer coatings on exposed surfaces of medical devices may flake off or otherwise be damaged during delivery, thereby preventing the biologically or pharmacologically active substance from reaching the target site. Still further, drug impregnated polymer coatings are limited in the quantity of the biologically or pharmacologically active substance to be delivered by the amount of a drug that the polymer coating can carry and the size of the medical devices. Controlling the rate of elution using polymer coatings is also difficult.

Accordingly, drug-eluting medical devices that enable increased quantities of a biologically or pharmacologically active substance to be delivered by the medical device, and allow for improved control of the elution rate of the substance, and improved methods of forming such medical devices are needed. Further, drug-eluting medical devices that are capable of eluting multiple biologically or pharmacologically active substances or eluting substances is different directions are needed. Effective methods of forming such devices are also needed.

SUMMARY OF INVENTION

In an embodiment of a method of forming a stent, a composite member including an outer member and an hourglass shaped core member disposed within a lumen of the outer member is shaped into a stent pattern. Openings are formed through the outer member to the core member, either before or after shaping the composite member into the stent pattern. After shaping the composite member into the stent pattern, the composite member is processed such that the core member is removed from the outer member without adversely affecting the outer member, thereby leaving an outer member with an hourglass shaped lumen. The outer member is then swaged such that the hourglass shaped lumen is separated into a first lumen and a second lumen separated by a portion of the outer member. In some embodiments, the outer member can be swaged prior to removing the core member. The lumens may then be filled with a biologically or pharmacologically active substance(s).

In another embodiment of a method of forming a stent, a composite member including an outer member, an inner member disposed within a lumen of the outer member, and an intermediate member disposed between the outer member and the inner member is shaped into a stent pattern. Openings are formed through the outer member to the intermediate member, either before or after shaping the composite member into the stent pattern. After shaping the composite member into the stent pattern, the composite member is processed such that the intermediate member is removed from the outer member without adversely affecting the outer member or the inner member, thereby leaving the outer member and the inner member with a cavity disposed there between. The outer member is then swaged such that portions of the outer member are pressed into contact with the inner member, thereby deforming the outer member and forming a first lumen and a second lumen separated by the inner member and the portions of the outer member in contact with the inner member. The lumens may then be filled with a biologically or pharmacologically active substance(s).

In another embodiment of a method of forming a stent, a wire having an outer member and an internal support structure dividing an internal lumen of the wire into a plurality of lumens is shaped into a stent pattern. Openings are formed through the outer member to at least one of the lumens, either before or after the step of shaping the wire into the stent pattern. The plurality of lumens may then be filled with at least one biologically or pharmacologically active substance. The internal support structure may be t-shaped or cross shaped, honeycombed shaped, or a single dividing wall. The outer member may be round, rectangular, oval, or other shapes.

BRIEF DESCRIPTION OF DRAWINGS

The foregoing and other features and advantages of the invention will be apparent from the following description of the invention as illustrated in the accompanying drawings. The accompanying drawings, which are incorporated herein and form a part of the specification, further serve to explain

DETAILED DESCRIPTION OF THE INVENTION

Specific embodiments of the present invention are now described with reference to the figures, where like reference numbers indicate identical or functionally similar elements.

Figure 1:
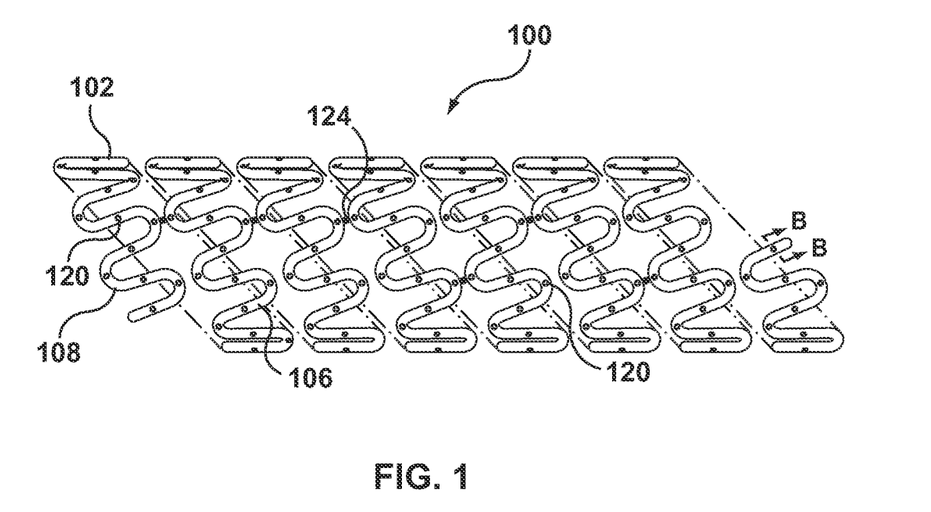
FIG. 1 is a schematic illustration of an embodiment of an exemplary stent.
Figure 2:
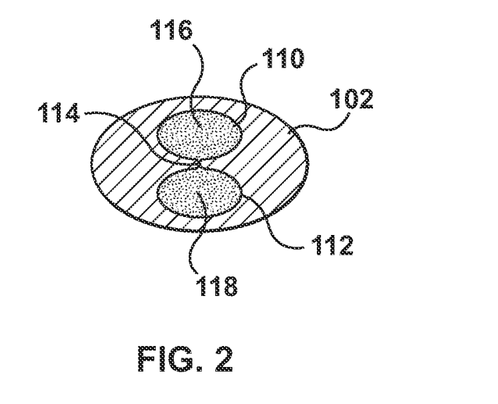
FIG. 2 is a cross-sectional view taken along line A-A of FIG. 1.
Figure 3:
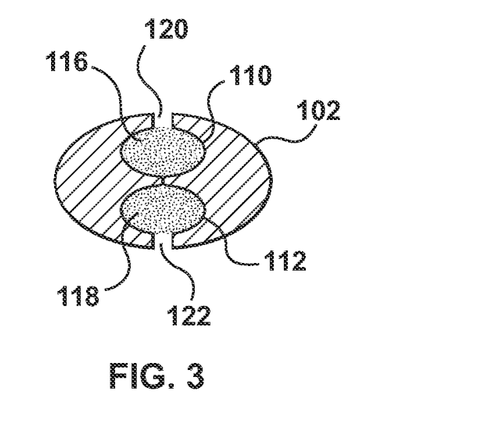
FIG. 3 is a cross-sectional view taken along line B-B of FIG. 1.

An embodiment of a stent 100 disclosed herein is shown in FIGS. 1-3. In the embodiment shown in FIG. 1, stent 100 is formed from a wire 102 bent or formed into a series of generally sinusoidal waves including generally straight segments or struts 106 joined by bent segments or crowns 108 and helically wrapped into a tube, as shown in FIG. 1. The term "wire" as used herein means an elongated element or filament or group of elongated elements or filaments and is not limited to a particular cross-sectional shape or material. In the embodiment shown in FIG. 1, selected crowns 108 of longitudinally adjacent sinusoids may be joined by, for example, fusion points 124. The invention hereof is not limited to the pattern shown in FIG. 1. Stent 100 can be formed into any pattern suitable for use as a stent. For example, and not by way of limitation, stent 100 can be formed into patterns disclosed in U.S. Pat. No. 4,800,882 to Gianturco, U.S. Pat. No. 4,886,062 to Wiktor, U.S. Pat. No. 5,133,732 to Wiktor, U.S. Pat. No. 5,782,903 to Wiktor, U.S. Pat. No. 6,136,023 to Boyle, and U.S. Pat. No. 5,019,090 to Pinchuk, each of which is incorporated by reference herein in its entirety. Further, instead of a single length of wire formed into a stent pattern, a plurality of wires may be formed into a two-dimensional waveform and wrapped into individual cylindrical elements. The cylindrical elements may then be aligned along a common longitudinal axis and joined to form the stent.

As shown in FIGS. 2 and 3, wire 102 of the completed stent 100 is hollow, allowing for a biologically or pharmacologically active substance to be deposited within lumens of hollow wire 102. In particular, FIG. 2 is a cross-sectional view of wire 102 taken along line A-A of FIG. 1 and FIG. 3 is a cross-sectional view of wire 102 taken along line B-B of FIG. 1. Wire 102 has a generally oblong shape and includes two lumens 110, 112. FIG. 2 shows wire 102 at a location without openings 120, 122, while FIG. 3 shows wire 102 at a location with openings 120, 122 leading to lumens 110, 112, respectively. Lumens 110, 112 are separated by a divider 114 that is formed from portions of outer member 102, as will be described in more detail below. A first biologically or pharmacologically active substance 116 is disposed in lumen 110 and a second biologically or pharmacologically active substance 118 is disposed in lumen 112. First biologically or pharmacologically active substance 116 and second biologically or pharmacologically active substance 118 may be the same or different. In the embodiment of FIGS. 1-3, opening 120 is directed outwardly or toward the abluminal surface of the stent and opening 122 is directed inwardly or toward the luminal surface of the stent. However, openings 120, 122 may be provided anywhere along the circumference of wire 102 and need not be aligned as shown in FIG. 3. Openings 120, 122 are dispersed along the length of the stent and through the wall of hollow wire 102 to permit biologically or pharmacologically active substances 116, 118 to be released from lumens 110, 112. Openings 120, 122 may be disposed only through struts 106 of stent 100, only through crowns 108 of stent 100, or through both struts 106 and crowns 108. Openings 120, 122 may be sized and shaped as desired to control the elution rate of biologically or pharmacologically active substances 116, 118 from stent 100. Larger sized openings generally permit a faster elution rate and smaller sized openings generally provide a slower elution rate. Further, the size and/or quantity of openings 120, 122 may be varied along stent 100 in order to vary the quantity and/or rate of biologically or pharmacologically active substances 116, 118 being eluted from stent 100 at different portions of stent 100. Openings 120, 122 may be, for example and not by way of limitation, 5-30 µm in diameter. Openings 120, 122 may have a constant diameter through the depth or have a tapered or conical shape.

Figure 4:
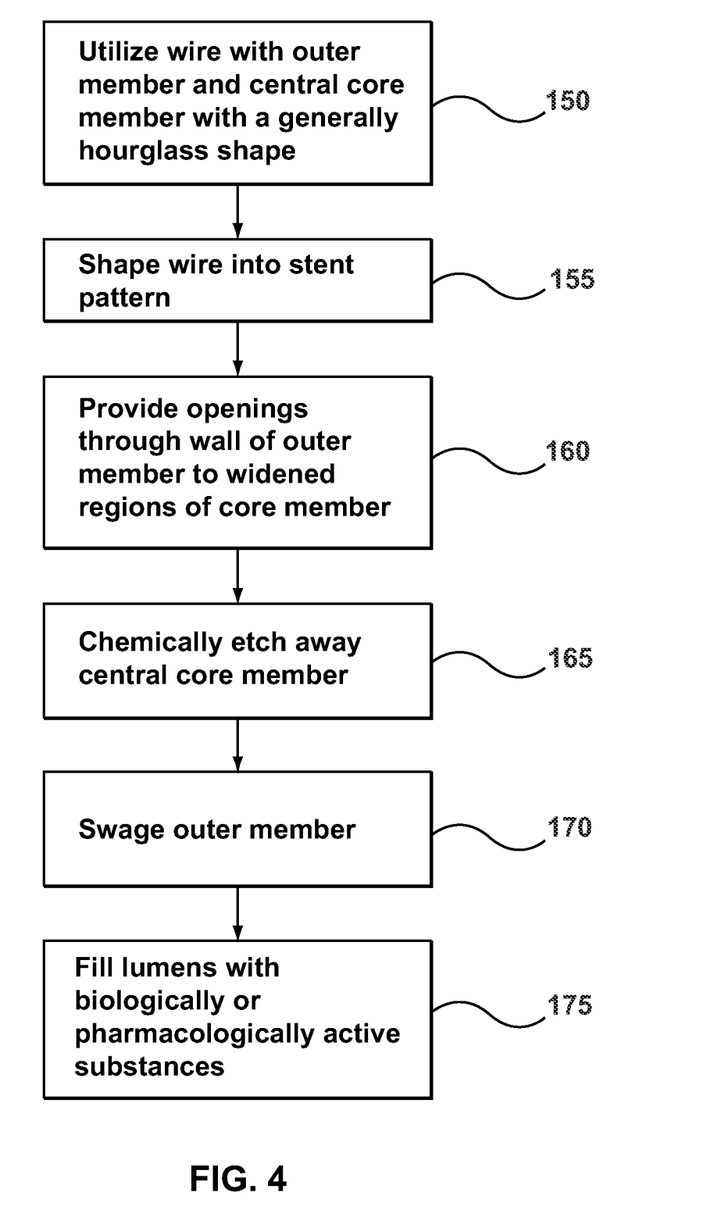
FIG. 4 is a flow chart of an embodiment of a method of forming a stent.
Figure 5:
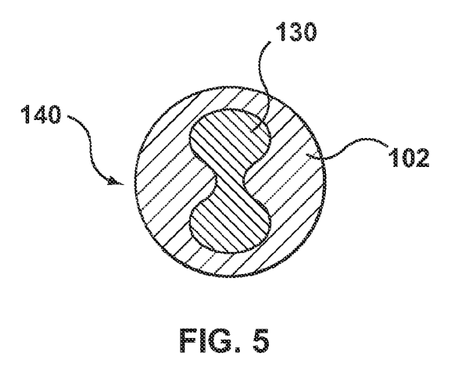
FIGS. 5-9 are schematic cross-sectional views of a wire illustrating the wire at stages of the method of FIG. 4.

FIGS. 4-9 show schematically an embodiment of a method of making the stent 100 of FIG. 1 having the wire 102 of FIGS. 2-3. As shown in FIG. 4 step 150 is to utilize a wire with an outer member and a central core member. These types of wire are sometimes referred to as core wires and may also be referred to as composite members. Core wire 140 hereof is formed of an outer member 102 and an inner or core member 130, as shown schematically in FIG. 5. Outer member 102 becomes hollow wire 102 of stent 100, and thus has been labeled with the same reference number. In this embodiment, inner member 130 is barbell or hourglass shaped, as seen in FIG. 5. Core wire 140 may be formed by any method known in the art, for example and not by way of limitation, a drawn filled tubing process, extruding the outer member over the inner member, or any other suitable method. Core wires with barbell or hourglass shaped inner members are available from Ft. Wayne Metals of Ft. Wayne, Ind.

Outer member 102 can be any material that is suitable to be used as a stent. Outer member 102, as explained in more detail below, is the surviving material that will become hollow wire 102. For example and not by way of limitation, outer member 102 may be a stainless steel, "MP35N", "MP20N", nickel titanium alloys such as Nitinol, magnesium, L605, or combinations thereof. "MP35N" and "MP20N" are trade names for alloys of cobalt, nickel, chromium and molybdenum available from Standard Press Steel Co., Jenkintown, Pa. "MP35N" generally consists of 35% cobalt, 35% nickel, 20% chromium, and 10% molybdenum. "MP20N" generally consists of 50% cobalt, 20% nickel, 20% chromium, and 10% molybdenum. The requirements for the material of outer member 102 are that it be biocompatible, sufficiently resilient to be used as a stent, and that it survives the process for eliminating core member 130, as discussed in more detail below.

Core member 130 may be a material that provides sufficient support to outer member 102 while the core wire is being bent into the stent pattern, as explained in more detail below. Core member 130 may be made of a material that is more ductile than the material of outer member 102. Further, core member 130 is made of a sacrificial material that can be removed by a process that does not damage the material of outer member 102. Examples of materials for core member 130 include, but are not limited to, tantalum (Ta), tungsten (W), molybdenum (Mo), niobium (Nb), rhenium (Re), carbon (C), germanium (Ge), silicon (Si) and alloys thereof.

A cross-section of core wire 140 is shown in FIG. 5. Outer member 102 may have an outer diameter in the range of 0.002 inch to 0.010 inch. In the embodiment shown, the wall thickness of outer member varies due to barbell or hourglass shaped core member 130. Further, the range for outer diameter noted above is merely an example and other diameters may be used depending on, for example, the material used, the desired stent shape, and the purpose or location of the stent.

Referring to FIG. 4, step 155 is to shape the core wire 140 into the stent pattern. As discussed above, the stent pattern can be the pattern shown in FIG. 1 or any other suitable pattern formed from a wire. Further, although the order of all the steps is not critical, step 155 should be done prior to removing core member 130 (i.e., step 165 explained in more detail below). Shaping core wire 140 into the stent pattern while core member 130 is disposed within outer member 102 helps prevent kinking or other deformations from occurring in outer member 102. Shaping the core wire 140 into the stent pattern shown in FIG. 1 generally includes the steps of forming core wire 140 into a two dimensional waveform followed by wrapping the waveform around a mandrel, as known to those skilled in the art. The end result is a helical stent pattern formed onto a mandrel. Selected crowns 108 of the helical pattern may then be fused or laser fused together and the stent may be removed from the mandrel. Methods for forming core wire 140 into a waveform may include, but are not limited to, the methods described in U.S. application Ser. No. 12/428, 581, filed Apr. 23, 2009, which is incorporated by reference herein in its entirety, or passing the core wire through gears such as those disclosed in U.S. Pat. No. 2,153,936 issued to Owens et al., which is also incorporated by reference herein in its entirety. Other methods for forming a wire into a waveform and for helically wrapping the waveform into a tube may be used, as known to those skilled in the art.

Figure 6:
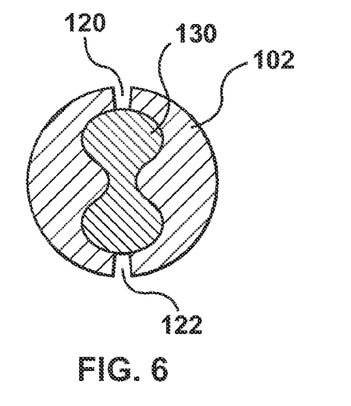

Step 160 shown in FIG. 4 is to provide openings 120, 122 through outer member 102. Openings 120, 122 may be laser cut, drilled, etched, or otherwise provided through outer member 102. Step 160 need not be performed after step 155, nor before step 165, although in some instances it is preferred to be before step 165, as explained in more detail below. If step 160 is performed after step 155, a cross-section of core wire 140 will include outer member 102, inner member 130, and openings 120, 122, as shown in FIG. 6.

Figure 7:
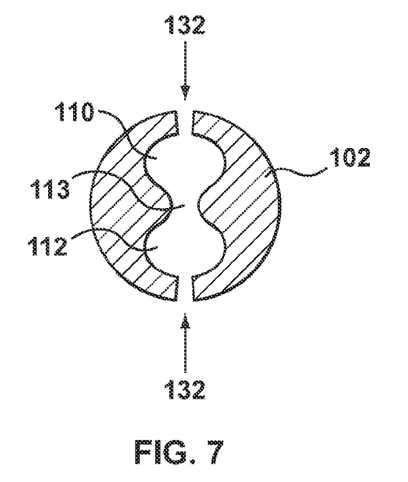

Step 165 is to etch away core member 130. Step 165 can be performed by any suitable process for removing core member 130 while preserving outer member 102. In particular, if outer member 102 is made from MP35N and inner member 130 is made from tantalum, subjecting core wire 140 to xenon difluoride ($XeF_2$) gas at low pressure 1-6 Torr) and relatively high temperature (approximately 110 to 150° C.) causes the xenon difluoride ($XeF_2$) gas to react with the tantalum (Ta) core member 130 to form $TaF_5$ and Xe gases, which can be exhausted from lumens 110, 112. Xenon difluoride ($XeF_2$) gas reacts similarly with a core member 130 made from tungsten, molybdenum, niobium, rhenium, carbon, germanium, and silicon. However, xenon difluoride ($XeF_2$) gas does not react with an outer member 102 formed of MP35N. Accordingly, after step 165 is completed, outer member 102 remains and core member 130 has been removed, leaving the structure shown in FIG. 7. As noted above, openings 120, 122 do not need to be formed prior to the step of removing core member 130 as long as there is a way to expose core member 130 to the etchant. For example, ends of the wire may be open or temporary ports may for formed through outer member 102 to expose core member 130 to the etchant. Removing core member 130 leaves outer member 102 and an hourglass or barbell shaped cavity including a narrow cavity region 113 and two larger cavity regions 110, 112, as shown in FIG. 7. Other examples of suitable outer member/core member combinations and methods for removing core members are described in co-pending U.S. application Ser. No. 12/500, 359, filed Jul. 9, 2009 and co-pending U.S. application Ser. No. 12/884,551, filed Sep. 17, 2010, each of which is incorporated by reference herein in its entirety. For example, and not by way of limitation, methods such as wet chemical dissolution, solubilization, sublimation, and melting may be used with appropriate outer member/core member combinations.

Figure 8:
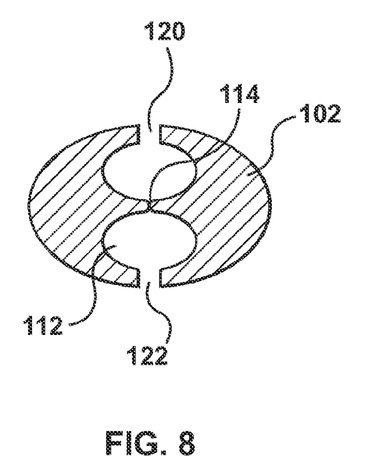

After core member 130 has been removed, in step 170 the remaining outer member 102 may swaged or pressed in the direction of arrows 132 as indicated in FIG. 7. Outer member 102 may be swaged by any method or device known to those of ordinary skill in the art. For example, and not by way of limitation, methods and devices described in U.S. Published Patent Application Publication No. 2002/0065548 to Birdsall et al., which is hereby incorporated by reference herein in its entirety, may be utilized. Swaging of outer member 102 causes the outer member 102 to deform, such as by plastic deformation, into a generally elliptical or oval shape, as shown in FIG. 8. As the outer member 102 is deformed, portions of the outer member 102 at the narrow cavity region 113 of the hourglass or barbell shaped cavity come together to form a barrier 114 between the two larger cavity regions 110, 112, as also shown in FIG. 8. Barrier 114 creates two separate cavities or lumens 110, 112 in outer member 102. Outer member 102 may be heat treated during or after the swaging step in order to fuse or seal barrier 114 because barrier 114 is formed from different portions of outer member 102 coming together.

Figure 9:
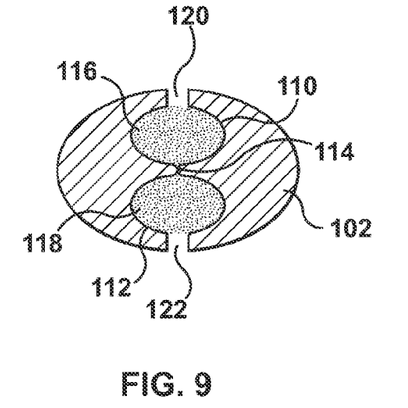

After core member 130 has been removed, lumens 110, 112 may be filled with first and second biologically or pharmacologically active substances 116, 118, respectively, as shown in step 175 of FIG. 4. This produces a hollow wire or outer member 102 with biologically or pharmacologically active substances 116, 118 disposed in lumens 110, 112 thereof, and openings 120, 122 through which biologically or pharmacologically active substances 116, 118 may be eluted, as shown in FIG. 9, as well as in FIGS. 2-3. Lumens 110, 112 may be filled with biologically or pharmacologically active substances 116, 118 by the methods described in co-pending U.S. application Ser. Nos. 12/884,503; 12/884,578; 12/884,362; 12/884,451; 12/884,596; and 12/884,501, each filed Sep. 17, 2010, each of which is incorporated by reference herein in its entirety, or any other suitable method known to those skilled in the art.

As noted above, the steps shown in FIG. 4 need not be performed in the exact order shown. For example, and not by way of limitation, core wire 140 may be swaged as shown in step 170 prior to removing core member 130. In such an embodiment, core member 130 must be sufficiently soft so as to permit the force from the swaging step (as shown by arrows 132) to displace the narrow region of core member 130 into two portions. For example, and not by way of limitation, a core member 130 made using tantalum may be utilized in such an embodiment. In such an embodiment, openings 120, 122 may be formed through outer member 102 after the swaging step. After forming openings 120, 122, or before if openings 120, 122 are not used to expose core member 130 to the etchant, core wire 140 is exposed to an etchant to remove core member 130. The embodiment described performs the steps 150-175 of FIG. 4 in the order of step 150, step 155, step 170, step 160, step 165, and step 175. Similarly, if core wire 140 is swaged with core member 130 in place, then core wire 140 may be swaged prior to shaping the core wire into the stent pattern. Thus, for example, the steps may be performed in the order of step 150, step 170, step 155, step 160, step 165, and step 175. Those skilled in the art recognize variations in the order of the steps, provided that the core wire 140 is shaped into the stent pattern prior to core member 130 being removed.

Figure 10:
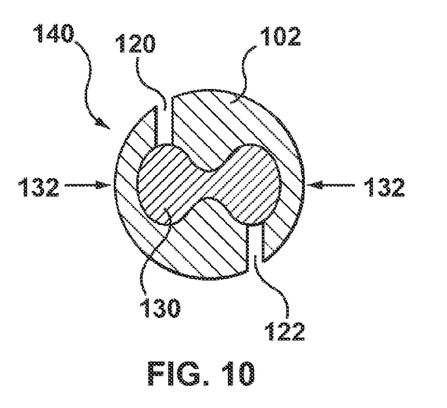
FIGS. 10-11 are schematic cross-sectional views of a wire illustrating the wire at certain stages of an embodiment method of forming the wire into a stent.
Figure 11:
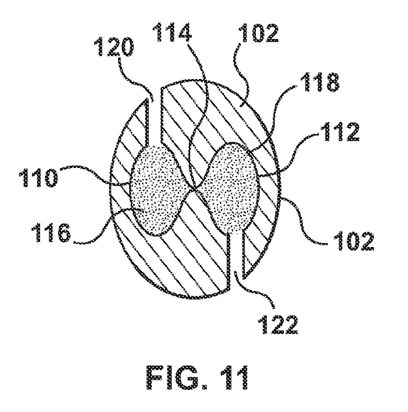
Figure 12:
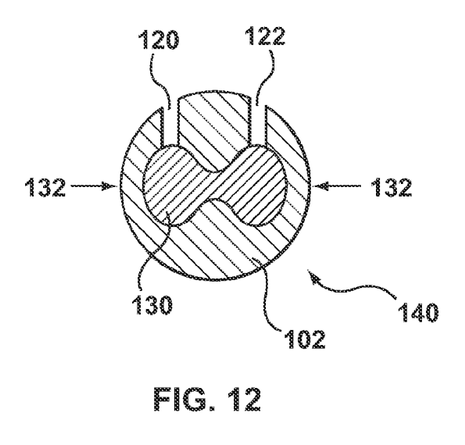
FIGS. 12-13 are schematic cross-sectional views of a wire illustrating the wire at certain stages of an embodiment method of forming the wire into a stent.
Figure 13:
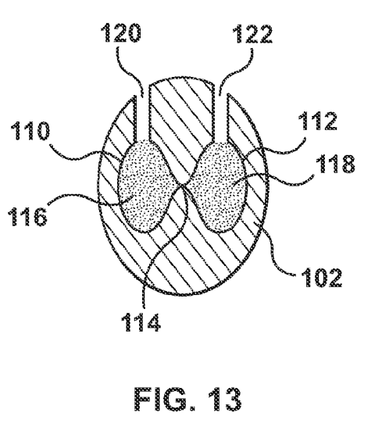

FIGS. 10-11 show another embodiment in which hourglass shaped core member 130 is oriented laterally, rather than vertically, with respect to the longitudinal axis of core wire 140, as shown in FIG. 10. Using the steps described above with respect to FIGS. 4-9, an outer member 102 with two lumens 110, 112 filled with first and second biologically or pharmacologically active substances 116, 118 with openings 120, 122 directed to inner and outer surfaces of the stent is formed, as shown in FIG. 11. In order to compress core wire 140 laterally, it may be necessary to swage core wire 140 prior to forming core wire 140 into the waveform or the core wire may be swaged as it is being formed into the waveform. FIGS. 12-13 are similar to FIGS. 10-11 except that the openings 120, 122 are in the same direction, rather than opposite directions as in FIGS. 10-11. Openings 120, 122 may be in opposite directions as shown in FIGS. 10-11 in order to provide different first and second biologically or pharmacologically active substances 116, 118 to the abluminal and luminal surfaces of the stent. Openings 120, 122 may be in the same general direction as shown in FIGS. 12-13 to provide different first and second biologically or pharmacologically active substances to the same abluminal (as in FIGS. 12-13) or luminal surface of the stent, to provide the same biologically or pharmacologically active substance to the surface at different times, or any other combination or reason known to those skilled in the art.

Figure 14:
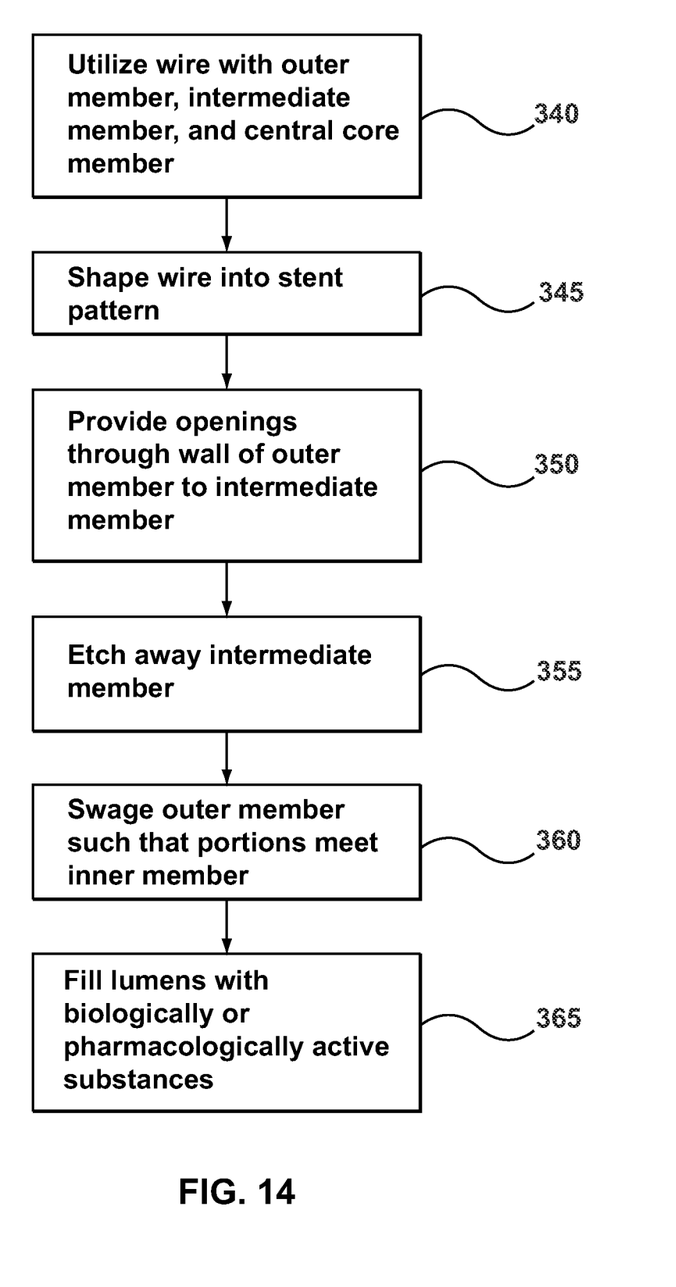
FIG. 14 is a flow chart of an embodiment of a method of forming a stent

FIGS. 14-19 show schematically another embodiment of a method of making a stent of FIG. 1 with multiple lumens with biologically or pharmacologically active substances disposed therein. As shown in FIG. 14, step 240 is to utilize a wire 300 with an outer member 302, an intermediate member 304, and a central core member 306, as shown in a schematic cross-section in FIG. 15. Wire 300 with multiple layers may be formed by any method known in the art, for example and not by way of limitation, a drawn filled tubing process, extruding the intermediate and outer members over the inner member, or any other suitable method. Wires with multiple layers as shown in FIG. 5 are available from Ft. Wayne Metals of Ft. Wayne, Ind.

Figure 15:
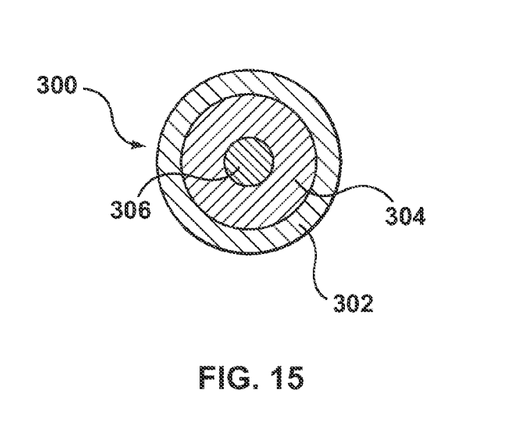
FIGS. 15-19 are schematic cross-sectional views of a wire illustrating the wire at stages of the method of FIG. 14.

In the example shown in FIG. 15, inner member 306 may have an outer diameter in the range of 0.0002 inch-0.005 inch. Intermediate member 304 may have an inner diameter in the range of 0.0002 inch-0.008 inch and an outer diameter in the range of 0.0015 inch-0.008 inch. Outer member may have an inner diameter in the range of 0.002 inch-0.008 inch and an outer diameter in the range of 0.002 inch-0.010 inch. In a non-limiting example, inner member 306 may have outer diameter of about 0.0005 inch, intermediate member 304 may have an outer diameter of about 0.0015 inch, and outer member 302 may have an outer diameter of about 0.003 inch. Although wire 300 and outer, intermediate, and inner members 302, 304, 306 are shown as generally circular, those skilled in the art would recognize that other shapes may be utilized and the wall thicknesses noted above (i.e., the difference between outer and inner diameters) could be utilized. Further, the sizes noted above are merely examples, and those skilled in the art would recognize that various sizes may be utilized depending on the desired location the stent is to be placed, the materials used, the desired size of the lumens, and other factors.

Outer member 302 can be any material that is suitable to be used as a stent. Outer member 302, as explained in more detail below, is the surviving material that, together with inner member 306, will form the struts of a stent. For example and not by way of limitation, outer member 302 may be a stainless steel, MP35N, MP20N, nickel titanium alloys such as Nitinol, magnesium, L605, or combinations thereof. The requirements for the material of outer member 302 are that it be biocompatible, sufficiently resilient to be used as a stent, and that it survives the process for eliminating intermediate member 304, as discussed in more detail below.

Inner member 306 may be made of any material that will not damage the biologically or pharmacologically active substances to be placed in the lumens formed, as explained in more detail below. Further, inner member 306 should also be made of a material that survives the process of eliminating intermediate member 304, as discussed in more detail below. Inner member 306 may be made of the same material as outer member 302.

Intermediate member 304 may be a material that provides sufficient support to outer member 302 while wire 300 is being bent into the stent pattern, as explained in more detail below. Intermediate member 304 may be made of a material that is more ductile than the material of outer member 302. Further, intermediate member 304 is made of a sacrificial material that can be removed by a process that does not damage the material of outer member 302 and inner member 306. Examples of materials for intermediate member 304 include, but are not limited to, tantalum (Ta), tungsten (W), molybdenum (Mo), niobium (Nb), rhenium (Re), carbon (C), germanium (Ge), silicon (Si) and alloys thereof.

In one particular non-limiting example, outer member 302 and inner member 306 are made from MP35N, and intermediate member 304 is made from tantalum.

Referring to FIG. 14, step 345 is to shape wire 300 into the stent pattern. As discussed above, the stent pattern can be the pattern shown in FIG. 1 or any other suitable stent pattern formed from a wire. Further, although the order of all the steps is not critical, step 345 should be performed prior to removing intermediate core member 304, as explained in more detail below. Shaping wire 300 into the stent pattern while intermediate member 304 is disposed between outer member 302 and inner member 306 helps prevent kinking or other deformations from occurring in wire 300. Shaping wire 300 into the stent pattern shown in FIG. 1 generally includes the steps of forming wire 300 into a two dimensional sinusoid pattern followed by wrapping the pattern around a mandrel, as known to those skilled in the art and described above. The end result is a helical stent pattern formed onto a mandrel. Selected crowns of the helical pattern may then be welded together and the stent may be removed from the mandrel.

Figure 16:
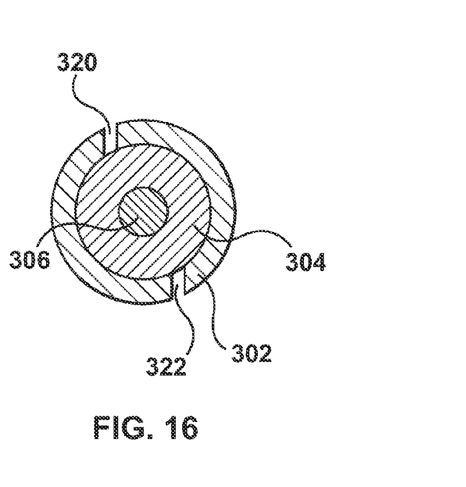

Step 350 shown in FIG. 14 is to provide openings 320, 322 through the wall of outer member 302 to intermediate member 304, resulting in the cross-section shown in FIG. 16. Openings 320, 322 may be laser cut, drilled, etched, or otherwise provided through outer member 302. Step 350 need not be performed after step 345, nor before step 355, although in some instances it is preferred to be before step 355, as explained in more detail below. If step 350 is performed after step 345, a cross-section of wire 300 will include outer member 302, intermediate member 304, core member 306, and openings 320, 322, as shown in FIG. 16. In the embodiment shown, openings 320, 322 are directed towards the abluminal and luminal sides of the stent, respectively. Those skilled in the art would recognize that openings 320, 322 may be directed any direction deemed suitable for the particular use of the stent. Further, there may be more openings dispersed around the circumference of the stent such that the substances within the lumens formed, as described in more detail below, may be eluted in any and/or all directions.

Step 355 is to etch away intermediate member 304. Step 355 can be performed by any suitable process for removing intermediate member 304 while preserving outer member 302 and inner member 306. In particular, if outer member 302 and inner member 306 are made from MP35N and intermediate member 304 is made from tantalum, subjecting wire 300 to xenon difluoride ($XeF_2$) gas at low pressure (1-6 Torr) and relatively high temperature (approximately 150° C.) causes the xenon difluoride ($XeF_2$) gas to react with the tantalum (Ta) intermediate member 304 to form $TaF_5$ and Xe gases, which can be exhausted from lumens 310, 312. Xenon difluoride ($XeF_2$) gas reacts similarly with an intermediate member 304 made from tungsten, molybdenum, niobium, rhenium, carbon, germanium, and silicon. However, xenon difluoride ($XeF_2$) gas does not react with an outer member 302 or inner member 306 formed of MP35N. However, as noted above, other examples of suitable outer member/intermediate member/inner member combinations and methods for removing intermediate members are described in co-pending U.S. application Ser. No. 12/500,359, filed Jul. 9, 2009 and co-pending U.S. application Ser. No. 12/884,551, filed Sep. 17, 2010, each of which is incorporated by reference herein in its entirety. For example, and not by way of limitation, methods such as wet chemical dissolution, solubilization, sublimation, and melting may be used with appropriate outer member/intermediate member/core member combinations. The intermediate member of the present embodiment would be the equivalent material of the core member described in the noted co-pending applications, and the inner member of the present embodiment would be the same as the outer member, or other suitable alternatives that would withstand the process described for removing the intermediate member.

Figure 17:
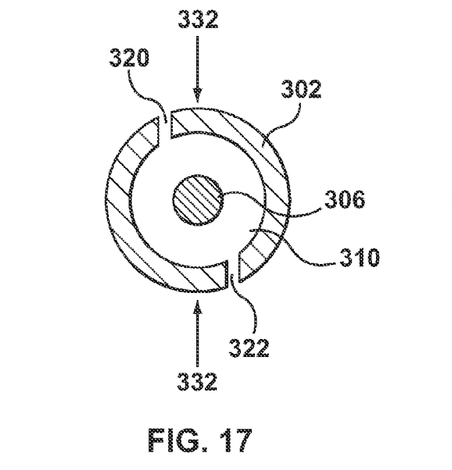

After step 355 is completed, outer member 302 and inner member 306 remain and intermediate member 304 has been removed, leaving the structure shown in FIG. 17. As noted above, openings 320, 322 do not need to be formed prior to the step of removing intermediate member 304 as long as there is a way to expose intermediate member 304 to the etchant. For example, ends of the wire may be open or temporary ports may for formed through outer member 302 to expose inner member 304 to the etchant. Removing intermediate member 304 leaves outer member 302 and inner member 306 with an annular lumen 308 disposed therebetween, as shown in FIG. 17. Inner member 306 may not be positioned at the center of the lumen of outer member 302 after intermediate member has been removed. Such movement of inner member 306 is acceptable. In some embodiments, it may be desirable to partially swage wire 300 prior to removing intermediate member 304 such that the inner member 306 is held in place after removal of the intermediate member 304.

Figure 18:
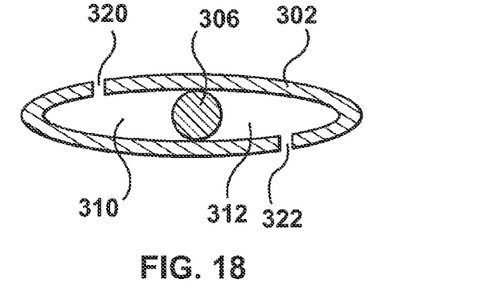

After intermediate member 304 has been removed, in step 360 the remaining outer member 302 and inner member 306 may be swaged or pressed in the direction of arrows 332 as indicated in FIG. 17. Wire 300 may be swaged by any method or device known to those of ordinary skill in the art. For example, and not by way of limitation, methods and devices described in U.S. Published Patent Application Publication No. 2002/0065548 to Birdsall et al., which is hereby incorporated by reference herein in its entirety, may be utilized. Swaging of wire 300 causes the outer member 300 to deform, such as by plastic deformation, into a generally elliptical or oval shape, as shown in FIG. 18. As the outer member 302 is deformed, the walls of the outer member 302 are pressed towards each other and contact inner member 306 to separate annular lumen 308 into two separate lumens 310, 312, as shown in FIG. 18. The portion where outer member 302 meets inner member 306 creates a barrier between the lumens 310, 312. The stent may be further treated, such as by annealing, during or after the swaging step to seal outer member 302 to inner member 306, if desired. FIG. 18 is not drawn to scale, and those skilled in the art would recognize the amount that outer member 302 is deformed to seal against inner member 306 depends on the diameter of inner member 306 and the thickness of intermediate member 304/annular lumen 308.

Figure 19:
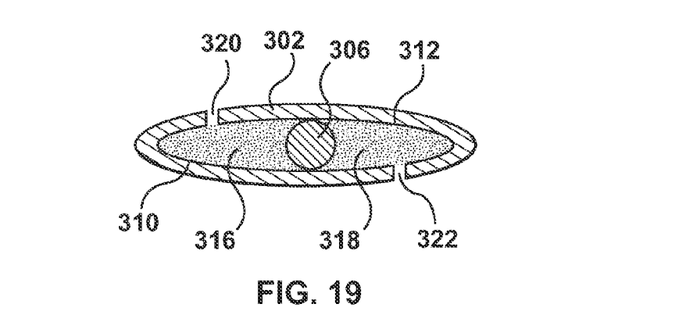

After step 360, lumens 310, 312 are filled first and second biologically or pharmacologically active substances 316, 318, as shown in step 365 of FIG. 14. Lumens 310, 312 may be filled with biologically or pharmacologically active substances 316, 318 by the methods described in co-pending U.S. application Ser. Nos. 12/884,503; 12/884,578; 12/884,362; 12/884,451; 12/884,596; and 12/884,501, each filed Sep. 17, 2010, each of which is incorporated by reference herein in its entirety, or any other suitable method known to those skilled in the art. This produces a hollow wire or outer member 302 with biologically or pharmacologically active substances 316, 318 disposed in lumens 310, 312 thereof, separated by inner member 306, and openings 320, 332 through which biologically or pharmacologically active substances 316, 318 may be eluted, as shown in FIG. 19.

First and second biologically or pharmacologically active substances 116, 118 or 316,318 may be the same or may be different. For example, and not by way of limitation, first biologically or pharmacologically active substance 116/316 may be an antiproliferative agent and opening 120/320 may be directed towards the outer, abluminal surface of the stent, and second biologically or pharmacologically active substance 118/318 may be an antithrombotic agent and opening 122/322 may be directed to the inner, luminal surface of the stent. In another example, first and second biologically or pharmacologically active substances 116/316, 118/318 may be the same or different substances configured to release at different times in vivo. The time release difference may be due to the substance itself, the size of the opening leading to the lumen, an additive, a biodegradable liner added to the lumen or opening, or other time release mechanisms know to those skilled in the art. Other combinations of first and second biologically or pharmacologically active substances may be utilized, as known to those skilled in the art.

FIGS. 20-26 show embodiments of cross-sections of generally hollow wires used to form a stent such as the stent shown in FIG. 1. In the embodiments of FIGS. 20-26, instead of utilizing a sacrificial material such as core member 130 or intermediate member 304 described above to support the wire during forming of the stent pattern, which requires removing the sacrificial material after forming the stent pattern, the wire includes an internal support structure to support the wire during formation of the stent pattern and internal lumen(s) to contain the biologically or pharmacologically active substance(s).

Figure 20:
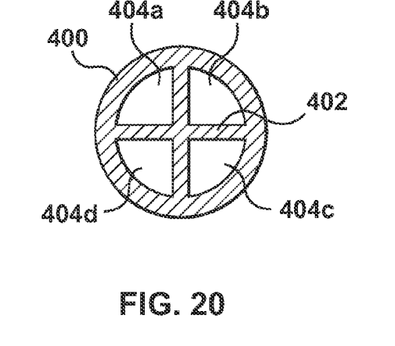
FIGS. 20-21 are schematic cross-sectional views of a portion of a hollow wire including a support structure disposed in the lumen of the hollow wire.
Figure 21:
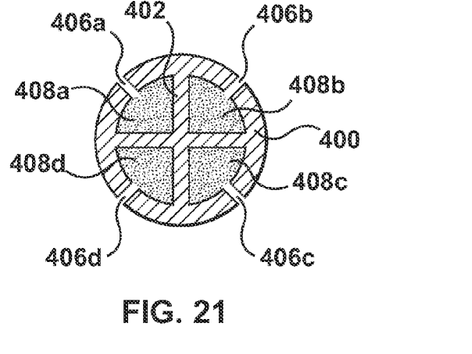

In particular, FIGS. 20-21 show a generally circular wire 400 including a t-shaped or cross-shaped internal wall 402 dividing the internal lumen of the wire 400 into four lumens 404a-404d. Wire 400 may be formed with internal wall 402 by co-extrusion or other methods known to those skilled in the art of wire formation. Wire 400 may be formed with internal wall 402 and a sacrificial material such as those described above in the lumens. The sacrificial material can be removed prior to forming the wire into the stent shape, leaving wire 400 with internal wall 403. Wire 400 is formed into a stent pattern, as explained above with respect to steps 155 and 245. Openings 406a-406d are disposed through the outer wall of wire 400 to lumens 404a-404d, respectively. Lumens 404a-404d are filled with biologically or pharmacologically active substances 408a-408d. The order of the steps described above may be varied. For example, lumens 404a-404d may be filled with biologically or pharmacologically active substances 408a-408d prior to forming wire 400 into a stent pattern. Similarly, openings 406a-406d may be formed prior to forming wire 400 into a stent pattern and the lumens may be filled after forming the wire into a stent pattern. Biologically or pharmacologically active substances 408a-408d may be the same or different, as explained above. Further, biologically or pharmacologically substances 408a-408d may be configured to elute at the same rate or different rates, as also explained above.

Figure 22:
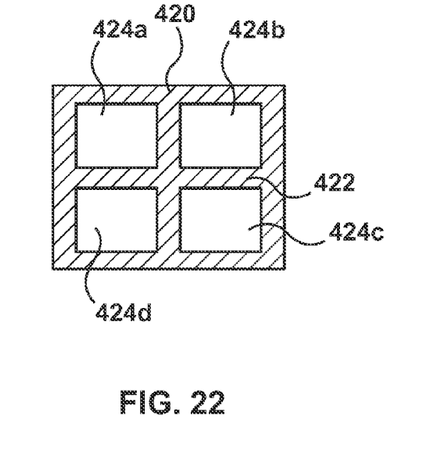
FIGS. 22-23 are schematic cross-sectional views of a portion of a hollow wire including a support structure disposed in the lumen of the hollow wire.
Figure 23:
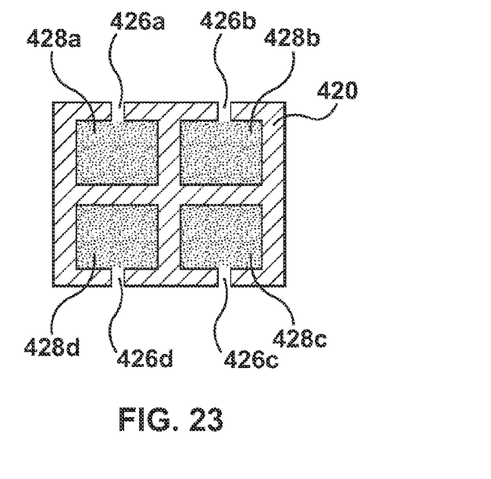

FIGS. 22-23 show a wire 420 similar to wire 400 except that wire 420 is generally rectangular in shape, including a t-shaped or cross-shaped internal wall 422 dividing the internal lumen of the wire 420 into four lumens 424a-424d. Wire 420 is formed into a stent pattern, as explained above with respect to steps 155 and 245. Openings 426a-426d are disposed through the outer wall of wire 420 to lumens 424a-424d, respectively. Lumens 424a-424d are filled with biologically or pharmacologically active substances 428a-428d. The order of the steps described above may be varied. For example, lumens 424a-424d may be filled with biologically or pharmacologically active substances 428a-428d prior to forming wire 420 into a stent pattern. Similarly, openings 426a-426d may be formed prior to forming wire 420 into a stent pattern and the lumens may be filled after forming the wire into a stent pattern. Biologically or pharmacologically substances 428a-428d may be the same or different, as explained above. Further, biologically or pharmacologically substances 428a-428d may be configured to elute at the same rate or different rates, as also explained above.

Figure 24:
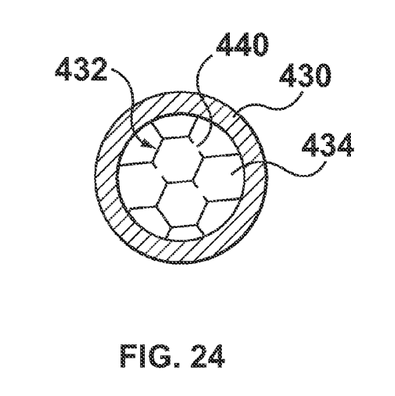
FIGS. 24-25 are schematic cross-sectional views of a portion of a hollow wire including a honeycomb support structure disposed in the lumen of the hollow wire.
Figure 25:
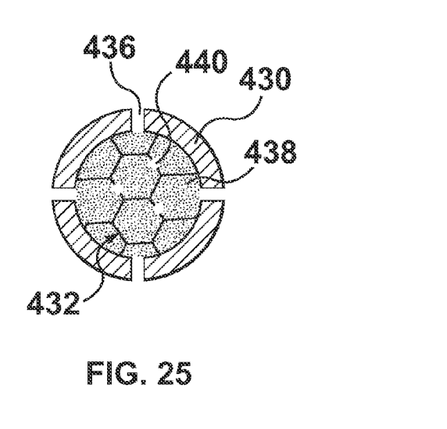

FIGS. 24-25 show a wire 430 similar to wire 400 except that wire 430 includes an internal honeycombed shaped structure 432 forming multiple internal lumens 434. Wire 430 may be formed with internal honeycomb shaped structure 432 by co-extrusion or other methods known to those skilled in the art of wire formation. Wire 430 is formed into a stent pattern, as explained above with respect to steps 155 and 245. Openings 436 are disposed through the outer wall of wire 430 to lumens 434. Lumens 434 are filled with biologically or pharmacologically active substances 438. Openings 440 through walls of internal honeycomb shaped structure 432 permits the biologically or pharmacologically active substances 438 to travel between internal lumens to be eluted from openings 436. A configuration such as the one shown in FIGS. 24-25 may also permit extending elution time. For example, and not by way of limitation, lumen 434a shown in FIG. 25 includes opening 436a through the outer wall of wire 430, as shown. Lumen 434b is adjacent to lumen 434a. Lumen 434b does not have access directly through the outer wall of wire 430. However, opening 440a in wall 432 between lumen 434a and 434b permits biologically or pharmacologically active substance 438 to travel from lumen 434b to lumen 434a. Similarly, lumen 434c does not have access through the outer wall of wire 430. However, opening 440b in the wall between lumen 434c and lumen 434b permits biologically or pharmacologically active substance 438 to travel from lumen 434c to lumen 434b, and subsequently to lumen 434a through opening 440a and outside of wire 430 through opening 436a. Such an elution pattern permits an extended drug elution, which may be desirable in some circumstances.

Although generally circular and rectangular wires have been described above, other shapes such as elliptical, oval, and other polygonal shapes may be used. Further, the internal supports described above may be varied or interchanged. For example, and not by way of limitation, the honeycomb internal structure described in FIGS. 24-25 may be used in a rectangular wire of FIGS. 22-23 or in other polygonal structures.

Figure 26:
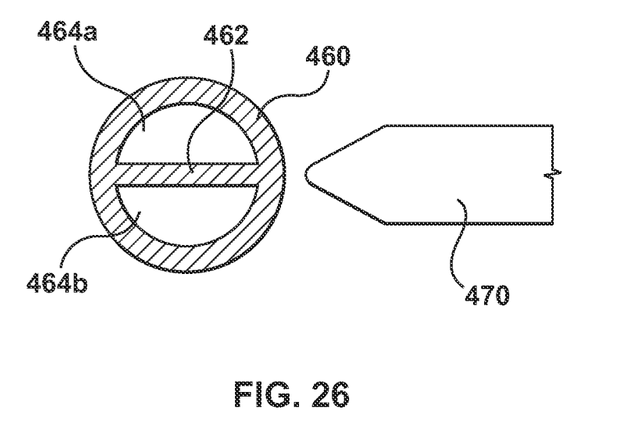
FIG. 26 is schematic cross-sectional view of a portion of a hollow wire including a support structure disposed in the lumen of the hollow wire.

Similarly, instead of a t-shaped or cross-shaped internal structure as shown in FIGS. 20-23, a single wall may be utilized that is oriented in the direction of fingers used to bend the wire, as described in more detail in U.S. application Ser. No. 12/428,581, filed Apr. 23, 2009, which is incorporated herein by reference in its entirety. Such a wire 460 with a single internal wall 462 dividing the lumen into two lumens 464a, 464b is shown in FIG. 26, with an exemplary finger 470 described in U.S. application Ser. No. 12/428,581, filed Apr. 23, 2009 shown.

Figure 27:
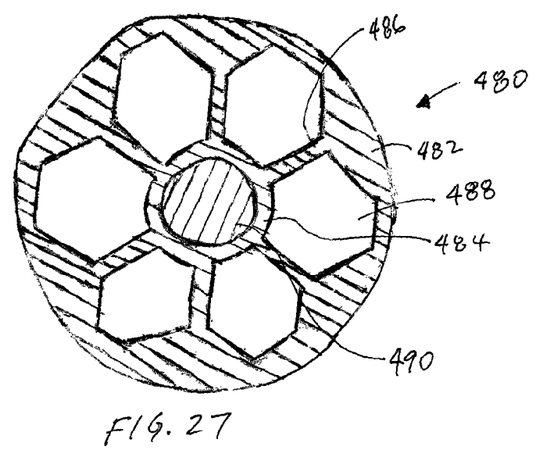
FIGS. 27-28 are schematic cross-sectional views of a portion of a wire including a core member and a honeycomb support structure.
Figure 28:
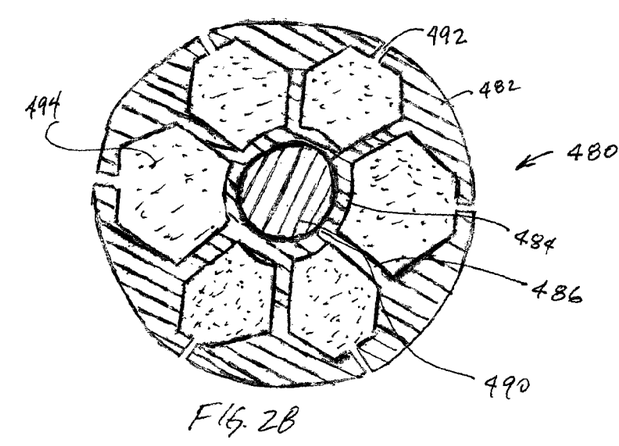

FIGS. 27-28 show a generally circular wire 480 including an outer member 482 and a core member 490. Outer member 482 includes an inner portion 484 that surrounds core member 490, and walls 486 extend radially outwards towards an outer surface of outer member 482. Lumens 488 are defined by outer member 482, inner portion 484, and walls 486. In the embodiment of FIGS. 27-28, there are six lumens 488 and a corresponding six walls 486, with two walls 486 defining each lumen 488, and two lumens 488 sharing each wall 486. The shape of lumens 488 in the embodiment of FIGS. 27-28 is generally honeycomb-shaped or hexagonal. Wire 480 may be formed by co-extrusion or other methods known to those skilled in the art of wire formation. Core member 490, inner portion 484 and walls 486 provide support to resist bending failure when forming wire 480 into a stent pattern, as described below. Core member 490 may be the same material as outer member 482 or may be a different material. In one non-limiting example, core member 490 may be more radiopaque than outer member 482 for improved visibility of the stent. For example, and not by way of limitation, outer member 482 (including inner portion 484 and walls 486) may be made from MP35N and core member may be made from tantalum, Wire 480 is formed into a stent pattern, as explained above with respect to steps 155 and 245. Openings 492 are disposed through outer member 482 to lumens 488. Openings 492 may be formed through outer member 482 to each of lumens 488 or may be formed through outer member 482 to access some of lumens 488 and additional openings may be formed in walls 486 such that lumens 488 without an opening 492 have access to lumens 488 with openings 492. Lumens 488 are filled with one or more biologically or pharmacologically active substances 494, as shown in FIG. 28. The order of the steps described above may be varied. For example, lumens 488 may be filled with biologically or pharmacologically active substances 494 prior to forming wire 480 into a stent pattern. Similarly, openings 492 may be formed prior to forming wire 480 into a stent pattern and the lumens may be filled after forming the wire into a stent pattern. Biologically or pharmacologically active substances 494 may be the same or different, as explained above. Further, biologically or pharmacologically substances 494 may be configured to elute at the same rate or different rates, as also explained above.

Further processing of the stents in the above-described embodiments, such as annealing, cleaning, and other processes known to those skilled in the art, can be performed at appropriate times in the methods described above. For example, and not by way of limitation, annealing the stent may take place before filling the stent with first and second biologically or pharmacologically active substances if the annealing step may damage the substances. Similarly, a final cleaning step may occur after filling the stent with the first and second biologically or pharmacologically active substances.

The term "biologically or pharmacologically active substance" refers to any substance, whether synthetic or natural, that has a pharmacological, chemical, or biological effect on the body or a portion thereof. Suitable biologically or pharmacologically active materials that can be used in embodiments of the present invention include without limitation glucocorticoids (e.g. dexamethasone, betamethasone), anti-thrombotic agents such as heparin, cell growth inhibitors, hirudin, angiopeptin, aspirin, growth factors such as VEGF, antisense agents, anti-cancer agents, anti-proliferative agents, oligonucleotides, antibiotics, and, more generally, antiplatelet agents, anti-coagulant agents, antimitotic agents, antioxidants, antimetabolite agents, and anti-inflammatory agents may be used. Antiplatelet agents can include drugs such as aspirin and dipyridamole. Aspirin is classified as an analgesic, antipyretic, anti-inflammatory and antiplatelet drug. Dipyridamole is a drug similar to aspirin in that it has anti-platelet characteristics. Dipyridamole is also classified as a coronary vasodilator. Anticoagulant agents may include drugs such as heparin, protamine, hirudin and tick anticoagulant protein. Anti-cancer agents may include drugs such as taxol and its analogs or derivatives. Taxol is also classified as a cell-growth inhibitor. Antioxidant agents may include probucol. Anti-proliferative agents may include drugs such as amlodipine, doxazosin, and sirolimus (rapamycin) or other—limus family compounds. Antimitotic agents and antimetabolite agents may include drugs such as methotrexate, azathioprine, vincristine, vinblastine, 5-fluorouracil, adriamycin and mutamycin. Antibiotic agents can include penicillin, cefoxitin, oxacillin, tobramycin, and gentamicin. Suitable antioxidants include probucol. Also, genes or nucleic acids, or portions thereof may be used. Such genes or nucleic acids can first be packaged in liposomes or nanoparticles. Furthermore, collagen-synthesis inhibitors, such as tranilast, may be used The stents described above may be used conventionally in blood vessels of the body to support such a vessel after an angioplasty procedure. It is known that certain biologically or pharmacologically active substances eluted from stents may prevent restenosis or other complications associated with angioplasty or stents. The stents may alternatively be used in other organs or tissues of the body for delivery of drugs to treat tumors, inflammation, nervous conditions, or other conditions that would be apparent to those skilled in the art.

While various embodiments of the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. Furthermore, there is no intention to be bound by any expressed or implied theory presented in the preceding technical field, background, brief summary or the detailed description. All patents and publications discussed herein are incorporated by reference herein in their entirety.

The invention claimed is:

1. A method of forming a stent comprising the steps of:
utilizing a composite member including an outer member, an inner member disposed within a lumen of the outer member, and an intermediate member disposed between the outer member and the inner member;
shaping the composite member into a stent pattern;
forming openings through the outer member to the intermediate member;
after the step of shaping the composite member into the stent pattern, processing the composite member such that the intermediate member is removed from the outer member without adversely affecting the outer member or the inner member, thereby leaving the outer member and the inner member with a cavity disposed therebetween; and
swaging the outer member such that portions of the outer member are pressed into contact with the inner member, thereby deforming the outer member into an elliptical or oval shape to form a first lumen and a second lumen, the first and second lumens separated by the inner member and the portions of the outer member in contact with the inner member.

2. The method of claim 1, further comprising the step of filling the first lumen with a first biologically or pharmacologically active substance and filling the second lumen with a second biologically or pharmacologically active substance after the core member has been removed.

3. The method of claim 2, wherein the first and second biologically or pharmacologically active substances are the same.

4. The method of claim 2, wherein the first and second biologically or pharmacologically active substances are different.

5. The method of claim 2, wherein the first and second biologically or pharmacologically active substances are selected from the group consisting of antineoplastic, antimitotic, antiinflammatory, antiplatelet, anticoagulant, anti fibrin, antithrombin, antiproliferative, antibiotic, antioxidant, and antiallergic substances as well as combinations thereof.

6. The method of claim 1, wherein the step of processing the composite member comprises exposing the composite member to an etchant that reacts with the intermediate member to remove the intermediate member, wherein the etchant does not react with the outer member and inner member.

7. The method of claim 6, wherein the etchant is a liquid chemical that dissolves the intermediate member.

8. The method of claim 6, wherein the etchant is a gas.

9. The method of claim 8, wherein the outer member and inner member are formed from MP35N, the intermediate member is formed from one of tantalum, tungsten, molybdenum, niobium, rhenium, carbon, germanium, and silicon, and the etchant is xenon difluoride.

10. The method of claim 6, wherein the intermediate member is soluble in the etchant and the outer member and inner member are not soluble in the etchant.

11. The method of claim 1, wherein the step of processing the composite member comprises heating the composite member to a temperature to sublimate the intermediate member.

12. The method of claim 1, wherein the step of processing the composite member comprises heating the composite member to a temperature to melt the intermediate member.

* * * * *